United States Patent
Orloff et al.

(10) Patent No.: US 11,395,630 B2
(45) Date of Patent: Jul. 26, 2022

(54) OCULAR DEVICES AND METHODS FOR THE EMPLOYMENT THEREOF

(71) Applicant: TearDX LLC, Bayside, NY (US)

(72) Inventors: Eugene Orloff, Bayside, NY (US);
Paul V. Braun, Champaign, IL (US);
Eleonora Orloff, Bayside, NY (US);
Yang Fei, New York, NY (US)

(73) Assignee: TearDX LLC, Bayside, NY (US)

( * ) Notice: Subject to any disclaimer, the term of this patent is extended or adjusted under 35 U.S.C. 154(b) by 0 days.

(21) Appl. No.: 15/947,127

(22) Filed: Apr. 6, 2018

(65) Prior Publication Data

US 2018/0289326 A1  Oct. 11, 2018

Related U.S. Application Data

(60) Provisional application No. 62/482,319, filed on Apr. 6, 2017.

(51) Int. Cl.
*A61B 5/1455* (2006.01)
*A61B 5/00* (2006.01)
(Continued)

(52) U.S. Cl.
CPC .............. *A61B 5/6821* (2013.01); *A61B 3/10* (2013.01); *A61B 3/101* (2013.01); *A61B 5/1455* (2013.01);
(Continued)

(58) Field of Classification Search
None
See application file for complete search history.

(56) References Cited

U.S. PATENT DOCUMENTS

| 4,597,392 A | 7/1986 | Opitz et al. |
| 6,850,786 B2 | 2/2005 | March |

(Continued)

FOREIGN PATENT DOCUMENTS

| BR | 102013007949 A2 | 6/2015 |
| CN | 101861135 A | 10/2010 |

(Continued)

OTHER PUBLICATIONS

P. Versura et al., "Performance of Tear Osmolarity Compared to Previous Diagnostic Tests for Dry Eye Diseases," Current Eye Research, 35(7), pp. 553-564, 2010 Informa Healthcare USA, Inc., ISSN: 0271-3683.

(Continued)

*Primary Examiner* — Marjan Fardanesh
(74) *Attorney, Agent, or Firm* — Kramer Levin Naftalis & Frankel LLP (57) ABSTRACT

An ocular device is disclosed along with methods for the employment thereof. In one aspect, a device for placement into a lacrimal punctum or conjunctival sac of a person includes one or more sensor materials responsive to one or more components of the chemical composition of the person's tears. Each sensor material is configured to present a tear-based color from a plurality of tear-based colors indicative of a medical condition of the person. In some embodiments, phenylboronic acid could be employed as a sensor material(s). In some embodiments, material(s) emitting radiation when excited by other radiation could be employed as a sensor material. In another aspect, methods for employing the ocular device are disclosed.

41 Claims, 8 Drawing Sheets

(51) Int. Cl.
  *A61B 3/10* (2006.01)
  *A61B 5/145* (2006.01)
(52) U.S. Cl.
  CPC ...... *A61B 5/14507* (2013.01); *A61B 5/14546* (2013.01)

(56) References Cited

U.S. PATENT DOCUMENTS

| | | | |
|---|---|---|---|
| 7,105,352 | B2 | 9/2006 | Asher et al. |
| 7,998,412 | B2 | 8/2011 | Burles et al. |
| 8,334,140 | B2 | 12/2012 | Kabilan et al. |
| 9,474,645 | B2 | 10/2016 | Cui et al. |
| 2005/0232972 | A1 | 10/2005 | Odrich |
| 2006/0226402 | A1 | 10/2006 | Kim et al. |
| 2007/0030443 | A1 | 2/2007 | Chapoy et al. |
| 2007/0154395 | A1 | 7/2007 | Morris et al. |
| 2009/0099626 | A1* | 4/2009 | de Juan, Jr. ........ G01R 33/0213 607/60 |
| 2009/0251693 | A1 | 10/2009 | Hu |
| 2010/0185066 | A1 | 7/2010 | March |
| 2010/0222657 | A1 | 9/2010 | Ibey et al. |
| 2011/0136929 | A1 | 6/2011 | Chow et al. |
| 2011/0286064 | A1 | 11/2011 | Burles et al. |
| 2011/0305872 | A1 | 12/2011 | Li et al. |
| 2011/0305881 | A1 | 12/2011 | Schultz et al. |
| 2011/0305898 | A1 | 12/2011 | Zhang et al. |
| 2012/0177576 | A1 | 7/2012 | Hu |
| 2012/0259188 | A1 | 10/2012 | Besling |
| 2013/0176530 | A1 | 7/2013 | Goodenough et al. |
| 2013/0258275 | A1 | 10/2013 | Toner et al. |
| 2013/0317133 | A1 | 11/2013 | Scales et al. |
| 2014/0343387 | A1 | 11/2014 | Pugh et al. |
| 2015/0061837 | A1 | 3/2015 | Honore et al. |
| 2015/0065905 | A1 | 3/2015 | Pugh |
| 2015/0087945 | A1 | 3/2015 | Ziaie et al. |
| 2015/0148648 | A1 | 5/2015 | Pugh |
| 2015/0148650 | A1 | 5/2015 | Pugh |
| 2015/0217129 | A1 | 8/2015 | Thomas et al. |
| 2015/0289790 | A1* | 10/2015 | Swenson ............ A61B 5/14517 600/344 |
| 2016/0003786 | A1 | 1/2016 | Daily et al. |
| 2016/0045144 | A1 | 2/2016 | Bansal et al. |
| 2016/0252505 | A1 | 9/2016 | Braun et al. |
| 2016/0361001 | A1 | 12/2016 | Tai et al. |
| 2017/0020390 | A1 | 1/2017 | Flitsch et al. |
| 2017/0086676 | A1 | 3/2017 | Flitsch et al. |

FOREIGN PATENT DOCUMENTS

| | | |
|---|---|---|
| CN | 102727218 A | 10/2012 |
| WO | WO 02/03855 A1 | 1/2002 |
| WO | WO 03/096876 A2 | 11/2003 |
| WO | WO2003096876 A2 | 11/2003 |
| WO | WO2015192064 A1 | 12/2015 |
| WO | WO2016015270 A1 | 2/2016 |
| WO | WO2016015270 A1 | 2/2016 |
| WO | WO2016115369 A1 | 7/2016 |
| WO | WO2016176252 A1 | 11/2016 |
| WO | WO2016205190 A1 | 12/2016 |
| WO | WO2017007819 A1 | 12/2017 |

OTHER PUBLICATIONS

Carolyn G. Begley et al., "Responses of Contact Lens Wearers to a Dry Eye Survey", Optometry and Vision Science, vol. 77, No. 1, Jan. 2000, pp. 40-46.
Tsung-Han Tsai et al., "Dynamic Gradient Directed Molecular Transport and Concentration in Hydrogel Films," Angewandte Chemie Int. Ed. 2017 Wiley-VCH Verlag GmbH & Co., KGaA, Weinheim, pp. 5001-5006.
Mark D.P. Willcox, PhD. et al., "TFOS Dews II Tear Film Report," The Ocular Surface 15, (2017 Elsevier Inc.), pp. 366-403.
Ulrike Stahl et al., "Osmolality and Tear Film Dynamics," 2011 Vision Co-operative Research Centre, Clinical and Experimental Optometry 2011 Optometrists Association Australia, Clin. Exp. Optom. 2012; 95: 1: pp. 3-11.
Ramachandram Badugu et al., "Contact Lens to Measure Individual Ion Concentrations in Tears and Applications to Dry Eye Disease," 2017 Elsevier Inc., Analytical Biochemistry 542 (2018) pp. 84-94.
Nicholas M. Farandos et al., "Contact Lens Sensors in Ocular Diagnostics," 2014 Wiley-VCH Verlag GmbH & Co. KGaA, Weinheim, Adv. Healthcare Mater. 2015, pp. 792-810.
Ali K. Yetisen et al., "Paper-based Microfluidic System for Tear Electrolyte Analysis," The Royal Society of Chemistry 2017, Lab Chip. 2017, 17, pp. 1137-1148.
Sandra Ast et al., "A Highly K+-Selective Phenylaza-[18]crown-6-Lariat-Ether-Based Fluoroionophore and Its Application in the Sensing of K+ Ions with an Optical Sensor Film and in Cells," 2013 Wiley-VCH Verlag GmbH & Co., KGaA, Weinheim, Chem. Eur. J. 2013, 19, pp. 14911-14917.
Daniel Harvey et al., "Fibre Optics Sensors in Tear Electrolyte Analysis: Towards a Novel Point of Care Potassium Sensor," Elsevier, Contact Lens & Anterior Eye 35 (2012) pp. 137-144.
Jason J. Nichols and Loraine T. Sinnott, "Tear Film, Contact Lens, and Patient-Related Factors Associated with Contact Lens-Related Dry Eye," Investigate Ophthalmology & Visual Science, Apr. 2006, vol. 47, No. 4, Association for Research in Vision and Ophthalmology, pp. 1319-1328.
Jeffrey P. Gilbard and Scott R. Rossi, "Changes in Tear Ion Concentrations in Dry-Eye Disorders," Cornea Research Unit, Schepens Eye Research Institute, Department of Ophthalmology, Harvard Medical School, Boston, MA, pp. 529-533.
Andrew G. Mayes et al., "Metal Ion-Sensitive Holographic Sensors," Institutue of Biotechnology, University of Cambridge, Cambridge, UK, 2002 American Chemical Society, Analytical Chemistry, vol. 74, No. 15, Aug. 1, 2002, pp. 3649-3657.
Guangjie Song et al., "A Highly Selective, Colorimetric, and Environment-Sensitive Optical Potassium Ion Sensor," ChemComm, The Royal Society of Chemistry 2017, vol. 53, No. 41, pp. 5602-5605.
Invitrogen by Thermo Fisher Scientific, Molecular Probes Handbook, "A Guide to Fluorescent Probes and Labeling Technologies," 11th Edition 2010, Chapter 21, Indicators for Na+, K+, Cl− and Miscellaneous Ions, pp. 903-922.
Ramachandram Badugu et al., "Boronic Acid Fluorescent Sensors for Monosaccharide Signaling Based on the 6-methoxyquinolinium Heterocyclic Nucleus: Progress Toward Noninvasive and Continuous Glucose Monitoring," Science & Direct, Elsevier, Bioorganic & Medicinal Chemistry vol. 13, 2005, pp. 113-119.
Matti Ben-Moshe et al., "Fast Responsive Crystalline Colloidal Array Photonic Crystal Glucose Sensors," Department of Chemistry, University of Pittsburgh, Analytical Chemistry, vol. 78, No. 14, Jul. 15, 2006, pp. 5149-5157.
Martin Mesch et al., "Functionalized Hydrogel on Plasmonic Nanoantennas for Noninvasive Glucose Sensing," ACS Photonics, 4th Physics Institute and Research Center SCoPE, University of Stuttgart, Germany, ACS Publications, 2015 American Chemical Society, vol. 2, pp. 475-480.
Huanfen Yao et al., "A Contact Lens with Embedded Sensor for Monitoring Tear Glucose Level," NIH Public Access, Author Manuscript, Biosens Bioelectron. Mar. 15, 2011, 26(7), pp. 3290-3296.
Cheng Chen, "Current and Emerging Technology for Continuous Glucose Monitoring," Academic Editors, Sensors 2017, 17, 182; doi:10.3390/s17010182, pp. 1-19.
Ramachandram Badugu et al., "Fluorescence Sensors for Monosaccharides Based on the 6-methylquinolinium Nucleus and Boronic Acid Moiety: Potential Application to Ophthalmic Diagnostics," HHS Public Access, Author Manuscript, Available in PMC Jun. 6, 2016; Talanta, Feb. 15, 2005; 65(3): 762-768.
Ali K. Yetisen et al., "Glucose-Sensitive Hydrogel Optical Fibers Functionalized with Phenylboronic Acid," Advanced Science News, 2017 The Authors. Published by Wiley-VCH Verlag GmbH & Co. KGaA, Weinheim, Adv. Mater. 2017 1606380, pp. 1-11.
Taira Kajisa et al., "Glucose-Responsive Hydrogel Electrode for Biocompatible Glucose Transistor," Provigate Inc., Department of (56) References Cited

OTHER PUBLICATIONS

Research and Development, Tokyo, Japan, Science and Technology of Advanced Materials, 2017, vol. 18, No. 1 pp. 26-33.
Graham J. Worsley et al., "Measurement of Glucose in Blood with a Phenylboronic Acid Optical Sensor," Journal of Diabetes Science and Technology, vol. 2, Issue 2, Mar. 2008, Diabetes Technology Society, pp. 213-220.
Ramachandram Badugu et al., "Noninvasive Continuous Monitoring of Physiological Glucose Using a Monosaccharide-Sensing Contact Lens," Center for Fluorescence Spectroscopy, Department of Biochemistry and Molecular Biology, Medical Biotechnology Center, University of Maryland School of Medicine, Baltimore, Maryland, Analytical Chemistry, vol. 76, No. 3, Feb. 1, 2004, pp. 610-618.
Angelika Domschke et al., "Initial Clinical Testing of a Holographic Non-Invasive Contact Lens Glucose Sensor," Diabetes Tecnology & Therapeutics, vol. 8, No. 1, 2006, Mary Ann Liebert, Inc., pp. 89-93.
Satyamoorthy Kabilan et al., "Glucose-Sensitive Holographic Sensors," ResearchGate, Journal of Molecular Recognition 2004; 17: pp. 162-166, DOI:10.1002/jmr.663, Institute of Biotechnology, Cambridge, UK.
Jin Zhang, Ph.D. et al., "Noninvasive Diagnostic Devices for Diabetes through Measuring Tear Glucose," Journal of Diabetes Science and Technology, vol. 5, Issue 1, Jan. 2011, pp. 166-172.
Ramachandram Badugu et al., "Ophthalmic Glucose Sensing: A Novel Monosaccharide Sensing Disposable and Colorless Contact Lens," HHS Public Access, Department of Chemistry, University of Copenhagen, Author Manuscript, Analyst. Available in PMC Jun. 4, 2016; 129(6): 516-521. DOI: 10.1039/b314463c, pp. 1-20.
Jon Stefan Hansen et al., "Recent Advances in Fluorescent Arylboronic Acids for Glucose Sensing," Open Access, Biosensors, ISSN 2079-6374, Biosensors 2013, 3, pp. 400-418; DOI: 10.3390/bios3040400.
Ramachandram Badugu et al., "Ophthalmic Glucose Monitoring Using Disposable Contact Lenses," Center for Fluorescence Spectroscopy, Department of Biochemistry and Molecular Biology, pp. 363-397.
Ramachandram Badugu et al., "Ophthalmic Glucose Monitoring Using Disposable Contact Lenses—A Review," HHS Public Access, J Fluoresc. Author Manuscript ; available in PMC Jun. 13, 2016; Sep. 2004; 14(5): 617-633; pp. 1-37.
Ali K. Yetisen et al., "Reusable, Robust, and Accurate Laser-Generated Photonic Nanosensor," ACS Publications, 2014 American Chemical Society, Department of Chemical Engineering and Biotechnology, University of Cambridge, UK, dx.doi.org/10.1021/nl5012504, Nano Letters 2014, 14, pp. 3587-3593.
Research Notes, Implanted Optics, "Structure Regained in supercooled Liquid Silicon," 2004 Nature Publishing Group, Nature Materials, vol. 3, Issue 2, Feb. 2004, www.nature.com/naturematerials, p. 76.
Vladimir L. Alexeev et al., "Photonic Crystal Glucose-Sensing Material for Noninvasive Monitoring of Glucose in Tear Fluid," Automation and Analytical Techniques, American Association for Clinical Chemistry 2004, 50:12, pp. 2353-2360.
Suzanne Hagan et al., "Tear Fluid Biomarkers in Ocular and Systemic Disease: Potential Use for Predictive, Preventive and Personalised Medicine," EPMA Journal, 2016 7:15, DOI:10.1186/s13167-016-0065-3.
David Spero, BSN, RN, "Is Continuous Glucose Monitoring Worth It?" Diabetes Self-Management. N.p., Sep. 28, 2011. htttps://www.diabetesselfmanagement.com/blog/is-continuous-glucose-monitoring-worth-it/print/ pp. 1-3.
Justin T. Baca, Ph.D., et al., "Tear Glucose Analysis for the Noninvasive Detection and Monitoring of Diabetes Mellitus" Clinical Science, The Ocular Surface vol. 5 No. 4 (Oct. 2007): pp. 280-293. www.theocularsurface.com.
Jennifer D. Lane et al., "Tear Glucose Dynamics in Diabetes Mellitus" (2006) Current Eye Research, 31:11, 895-901, DOI:10.1080/02713680600976552.
Adam J. Paulsen et al., "Dry Eye in the Beaver Dam Offspring Study: Prevalence, Risk Factors, and Health-Related Quality of Life" NIH Public Access Author Manuscript, Am J Ophthalmol, Apr. 2014, 157(4): 799-806. DOI: 10.1016/j.ajo.2013.12.023.
Liqiang Zhang et al., "A Polymer-based Ratiometric Intracellular Glucose Sensor" The Royal Society of Chemistry 2014, RSC Publishing, Chemical Communications, Jul. 4, 2014, 50(52): 6920-6922.
Grant R. Hendrickson and L. Andrew Lyon, "Bioresponsive Hydrogels for Sensing Applications" The Royal Society of Chemistry 2009, Soft Matter, 2009, 5, 29-35. DOI: 10.1039/b811620b.
Gillian F. Whyte, "Molecular Recognition with Boronic Acids—Applications in Chemical Biology" Springer-Verlag Berlin Heidelberg 2013, J. Chem Biol (2013) 6:161-174. DOI: 10.1007/s12154-013-0099-0.
Qian Wu et al., "Organization of Glucose-Responsive Systems and Their Properties" Chemical Reviews, ACS Publications, 2011 American Chemical Society, dx.doi.org/10.1021/cr200027j, Chem. Rev. 2011, 111, 7855-7875.
Paul J. Beisswenger MD et al., "Glycated Proteins in Diabetes" Clinics in Laboratory Medicine, Diabetes Mellitus, ISSN 0272-2712, Mar. 2011, vol. 21(1):53-78, vi.
Dennis G. Hall, "Boronic Acids: Preparation and Applications in Organic Synthesis, Medicine and Materials" 2nd Ed. vol. 1-2. 2012, 1:1-134, 13:591-620, 14:621-676, v-xxi.
International Search Report PCT/US18/26464, dated Jul. 3, 2018.
Extended European Search Report Application No. 18781815.8 , dated Jul. 31, 2020.
Examination Report dated Mar. 17, 2021, European Patent Application No. 18781815.8-1113.
Chinese Office Action dated Apr. 2, 2021, Chinese Patent Application No. 201880023669.9.

* cited by examiner

OCULAR DEVICES AND METHODS FOR THE EMPLOYMENT THEREOF

CROSS-REFERENCE TO RELATED APPLICATION

This application claims priority to U.S. Provisional Application No. 62/482,319 entitled "Ocular Devices and Methods" filed on Apr. 6, 2017, which is hereby incorporated by reference herein in its entirety.

BACKGROUND

The present invention generally relates to new ocular devices and methods for diagnosing diseases and monitoring medical conditions.

Punctal plugs are ocular devices that may be inserted into the puncta (i.e., tear ducts) at the upper and/or lower eyelids to prevent drainage of basal tears, helping to treat for dry eye syndrome. These plugs are typically silicone-based, cause minimal-to-no irritation to the patient, and may be safely left in the puncta for years if not physically dislodged, providing a positive role in the treatment of patients suffering from dry eyes with little to no negative side effects.

Many medical conditions affect a large percentage of the human population. For example, diabetes is prevalent worldwide and a particularly troublesome disease to manage. Typically, to monitor current blood glucose levels, a diabetic must use a blood glucose meter and pierce or prick the skin (often on a finger) with a blood lancelet several times a day (e.g., up to 10 times a day). This can be expensive, inconvenient, painful, and intrusive. More recently, diabetics have the option of continuous glucose monitoring (CGM) by inserting one or more sensors under the skin such as, for example, in his or her arm or abdomen. These devices also require several daily finger-pricks for calibration and may cost thousands of dollars for the initial installation and subsequent maintenance of the sensors and batteries. See, e.g., Spero, David, "Is Continuous Glucose Monitoring Worth It?", Diabetes Self-Management, 28 Sep. 2011, which is hereby incorporated by reference herein in its entirety. Furthermore, the sensors could communicate with an external transmitter (e.g., a pager), adding complexity and cost to the monitoring system as well as introducing the potential for error.

It is generally known that a person's tears can be used to monitor various physiological and/or biochemical states (e.g., presence of vitamins, glucose level, etc.), and even to diagnose diseases. Similar to blood, tears are representative of the biochemical composition of the body. There are various kinds of tears including basal tears, reflex tears (e.g., resulting from exposure to tear gas), and psychic tears (e.g., released when crying). Basal tears are continually produced, and their components include, but are not limited to, glucose, minerals (e.g., iron), vitamins, neurotransmitters, metabolites, amino acids, urea, anti-oxidants, and many proteins and/or their associated metabolites. The correlation between blood glucose and basal tear glucose has been identified. See, e.g., Baca, Justin T., "Tear Glucose Analysis for the Noninvasive Detection and Monitoring of Diabetes Mellitus," The Ocular Surface, Vol. 5, No. 4, 2007, pp. 280-93; and Lane, Jennifer D., "Tear Glucose Dynamics in Diabetes Mellitus," Current Eye Research, 31:895-901, 2006 (Lane), both of which are hereby incorporated by reference herein in their entireties.

In recent years, mechanisms have been developed that analyze tears for protein biomarkers indicative of breast cancer through collection of basal tears followed by immunoassays. See, e.g., Daily, Anna, U.S. Patent Application Publication No. 2016/0003786 entitled "Methods of Detecting Cancer," which is hereby incorporated by reference herein in its entirety (Daily). Such mechanisms can include papers being inserted between a patient's eyeball and eyelid, lingering there during examination. These mechanisms can be inconvenient and expensive to use since the papers are usually administered in a laboratory setting and often require the patient being examined to remain in the laboratory for a period of time during the examination.

Mechanical stimulation of basal tears through the use of Schirmer test strips has also been done to measure glucose levels. Their efficacy, however, may be questionable since high glucose levels can be attributed to intercellular fluid leaking through conjunctival abrasion. Furthermore, testing glucose levels in this manner is intrusive and inconvenient much like with the frequent finger-pricks.

Other eye devices have also been proposed for CGM of non-stimulated tears including, for example, contact lenses having enzyme-based glucose electrodes (i.e., glucose oxidase) embedded therein. See, e.g., Honore, Frank, U.S. Patent Application Publication No. 2015/0061837 entitled "Reader Communication With Contact Lens Sensors and Display Device," which is hereby incorporated by reference herein in its entirety. Placing such components on contact lenses could be impractical, however, since the lenses can shift about the user's eyes and interfere with vision. Also, such contact lenses may not be practical for patients who do not otherwise use contact lenses or tolerate contact lenses due to, for example, prevalent dry eye conditions, which affect about 15% of Americans. See, e.g., Paulsen, Adam J., "Dry Eye in the Beaver Dam Offspring Study: Prevalence, Risk Factors, and Health-Related Quality of Life," American Journal of Ophthalmology, Vol. 157, Issue 4, Apr. 2014, pp. 799-806, which is hereby incorporated by reference herein in its entirety. Furthermore, the addition of monitoring devices to contact lenses may be costly for patients who prefer to use disposable contact lenses. Moreover, these devices may not provide sufficiently frequent monitoring of blood glucose levels. As such, there could be considerable complications and production costs involved with this small-scale technology.

Recently, designs based on phenylboronic acid (PBA) may be a replacement for glucose oxidase in CGM. See, e.g., Braun, Paul V. U.S. Patent Application Publication No. 2016/0252505 entitled "Volume Response Sensors Having Analyte Controlled Reversible Crosslinking," which is hereby incorporated by reference herein in its entirety (Braun). PBA-modified hydrogels (singularly, sensor material) may bind cis-diols in glucose, resulting in detectable fluorescent modification. See, e.g., Zhang, Liqiang, "A Polymer-Based Ratiometric Intracellular Glucose Sensor," Chemical Communications, Issue 52, 2014, pp. 6920-22; and Hendrickson, Grant R., "Bioresponsive hydrogels for sensing applications," Soft Matter, Issue 1, (2009), pp. 29-35, both of which are hereby incorporated by reference herein in their entireties.

Adaptable boronic acid chemistry could allow the sensor material to be customized across a wide range of glucose concentrations and even personalized for individual patients. Also, boronic acid derivatives have been utilized to track levels of sugars other than glucose as well as metal ions, nucleic acids, phospholipids, neurotransmitters (e.g. dopamine), and even Gram-Positive bacteria which concerns more so with eye-care diagnosis of bacterial infection (e.g., conjunctivitis or "Pink Eye") rather than monitoring of substance levels. See, e.g., Whyte, Gillian F., "Molecular recognition with boronic acids—applications in chemical biology," Journal of Chemical Biology, Vol. 6, Issue 4, Oct. 2013, pp. 161-74, which is hereby incorporated by reference herein in its entirety. Boronic acids can also be used to detect glycated-proteins (i.e., proteins bound to sugars), which are also known to be a monitorable marker for diabetes. See, e.g., Beisswenger, P. J., "Glycated Proteins in Diabetes," Clinics in Laboratory Medicine, 21, 2001, pp. 53-78, which is hereby incorporated by reference herein in its entirety.

Braun does not disclose employing the sensor material in tear analysis for a target compound (e.g., glucose). However, as described herein, such a sensor material may be adapted for the monitoring of medical conditions and diagnosing diseases since the color of the material can change depending on the concentration level of the target compound correlated to the condition or disease of interest.

Although the following discussion will be drawn to basal tears and basal tear glucose, there are numerous other medical conditions that require monitoring the presence of chemicals in the body such as the monitoring of iron level in anemic patients, the levels of vitamins, the presence of chemicals relating to kidney or liver function, etc. Unbalanced dopamine levels may, for example, contribute to mental illnesses such as schizophrenia and Parkinson's Disease.

Punctal plugs are particularly well-suited for adaptation with the sensor material, given that they are familiar to many patients and often remain in continual contact with a patient's tears for prolonged periods. These devices can thus be adapted as vehicles for the sensor material to provide a new gel-based disease monitoring and/or screening device as described herein. The high operational stability in PBA-hydrogels. See e.g., Hall, Dennis G., "Boronic Acids: Preparation and Applications in Organic Synthesis, Medicine and Materials," Wiley, 2nd ed., Vol. 1-2, Nov. 2011; and Wu, Qiao, "Organization of Glucose-Responsive Systems and Their Properties," Chemical Reviews, 111(12), Sep. 2011, pp. 7855-75, both of which are hereby incorporated by reference herein in their entireties), can also complement the long-term application of punctal plugs. Contact lenses can also be adapted as vehicles for the sensor material.

SUMMARY

Embodiments of the inventive concepts disclosed herein are directed to ocular devices and methods for the employment thereof to provide one with the ability to flexibly screen diseases and/or monitor a patient's medical conditions. An ocular device could include a sensor material, the color of which could change in response to a change in a patient's physiological and/or biochemical state represented in a chemical composition of tears. In some embodiments, the ocular device could be inserted or placed into a lacrimal punctum or conjunctival sac to accurately and safely detect the condition of interest. For example, the device could indirectly monitor blood glucose levels for a long time (e.g., up to several years) through monitoring of basal tear glucose levels. In some embodiments, the ocular device can include a punctal plug, a strip, or contact lens with the sensor material.

In one aspect, embodiments of the inventive concepts disclosed herein are directed to an ocular device, which may be comprised of a body, a first region located at a distal end of the body, and a first region located at a proximal end of the body. The body and the first region may be configured for insertion into a lacrimal punctum or conjunctival sac of a patient by qualified personal. In some embodiments, the second region could include one or more surfaces visible to an observer (e.g., the third-party observer or patient that is able to view his/her punctum or conjunctival sac). The surface(s) could be partially comprised of a sensor material configured to provide one or more tear-based colors. In some embodiments, the sensor material could be comprised of boronic acid configurable to change colors in response to a level of a patient's tear glucose or other compound of interest. The color of the surface(s) may provide the observer with an indication of a chemical composition of the patient's tears. In some embodiments, the second region could include sensor material that emits visible or near-infrared radiation of the electromagnetic spectrum when excited by a source of ultraviolet or visible radiation, where the one or more tear-based colors may correspond to one or more colors of radiation emitted when the sensor material is excited.

In another aspect, embodiments of the inventive concepts disclosed herein are directed to a system to employ the ocular device, which may include qualified medical personnel and the patient, where the ocular device may be inserted or placed into the punctum or conjunctival sac of the patient.

In another aspect, embodiments of the inventive concepts disclosed herein are directed to a method to employ the ocular device, which may include the qualified medical personnel or other medical personnel inserting or placing the ocular device into the punctum or conjunctival sac of the patient and observing the color of one or more surfaces of the device.

In another aspect, embodiments of the inventive concepts disclosed herein are directed to another method to employ the ocular device, which may a person such as qualified medical personnel observing an indication provided by the ocular device once it has been inserted or placed into the punctum or conjunctival sac of the patient and observing the color of emitted radiation from the device, for example, upon exciting the device with a particular radiation of the electromagnetic spectrum. In some embodiments, the emitted radiation may be visible or measurable through the close eyelid of the patient.

BRIEF DESCRIPTION OF THE DRAWINGS

The present invention is discussed in greater detail below with reference to exemplary embodiments illustrated in the accompanying drawings, in which.

DETAILED DESCRIPTION

In the following description, several specific details are presented to provide a thorough understanding of embodiments of the inventive concepts disclosed herein. One skilled in the relevant art will recognize, however, that embodiments of the inventive concepts disclosed herein can be practiced without one or more of the specific details, or in combination with other components, etc. In other instances, well-known implementations or operations are not shown or described in detail to avoid obscuring aspects of various embodiments of the inventive concepts disclosed herein.

Figure 1:
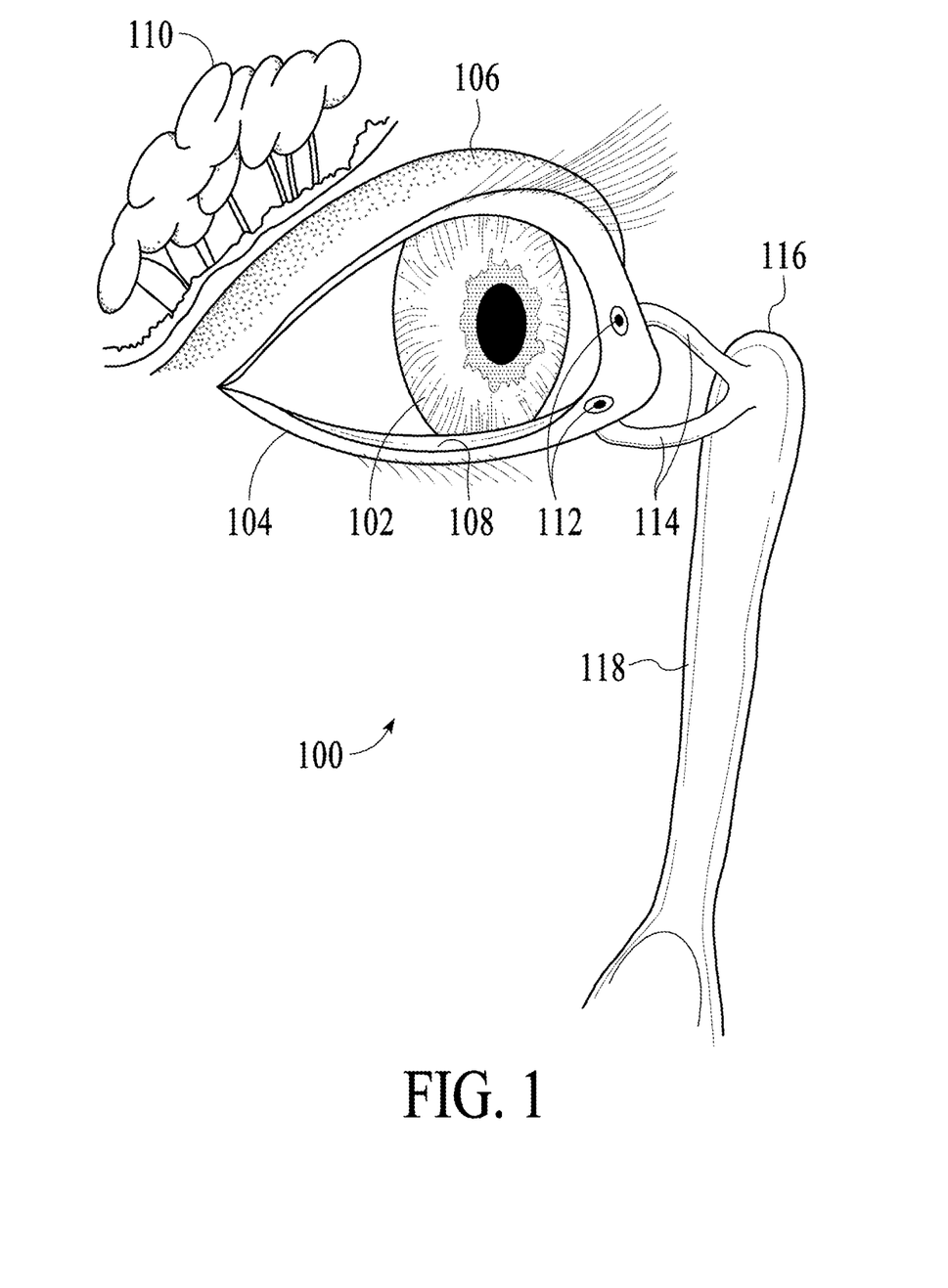
FIG. 1 illustrates a tear system of a person for tear production and drainage, in accordance with some embodiments.

Referring now to FIG. 1, the tear system 100 of a person for tear production and drainage is illustrated along with the human eye 102, a lower eyelid 104, and an upper eyelid 106; a conjunctival sac 108 is found between the human eye 102 and lower eyelid 104. The tear system 100 could include the lacrimal gland 110, lacrimal puncta 112, lacrimal ducts 114, lacrimal sac 116, and nasolacrimal duct 118. The lacrimal gland 108 secretes tears which are conveyed to the tail of the upper eyelid 104. Then, the tears pass over the surface of the eye 102 to the lacrimal puncta 112 (singularly, lacrimal punctum), small holes found in the inner corner of the upper and lower eyelids 104 and 106. The tears are then passed through the lacrimal ducts 114 to the lacrimal sac 116, before being passed into the nose via the nasolacrimal duct 118.

As discussed above, there are various kinds of tears including basal tears, reflex tears, and psychic tears. Basal tears are continually produced and include components of glucose, minerals, vitamins, neurotransmitters, metabolites, amino acids, urea, anti-oxidants, and many proteins and/or their associated metabolites.

Figure 2:
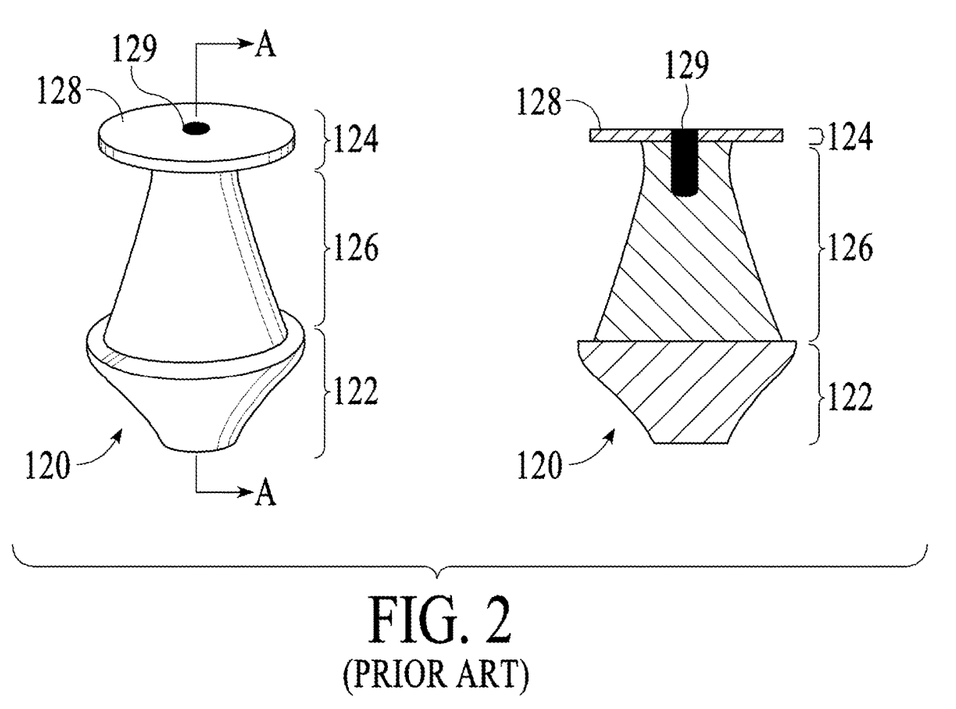
FIG. 2 illustrate perspective and cross-sectional views of a punctal plug, in accordance with some embodiments.

Referring now to FIG. 2, perspective and cross-sectional views of a punctal plug 120 representative of prior art is illustrated. As shown, the punctal plug may include a first region corresponding to a tail 122, a second region corresponding to a head 124, and a body corresponding to a shaft 126. An upper surface 128 of second region 124 could include a tool receptacle 129 to facilitate the use of an insertion/removal tool.

As discussed above, the punctal plug 120 has been used to treat dry eye syndrome as disclosed, for example, by Freeman in U.S. Pat. No. 3,949,750 entitled "Punctum Plug and Method for Treating Keratoconjunctivitis Sicca (Dry Eye) and Other Ophthalmic Aliments Using Same," and Herrick et al. in U.S. Pat. No. 4,660,546 entitled "Method for Treating for Deficiency of Tears," both of which are hereby incorporated by reference herein in their entireties. More recently, plugs have also been used for the administration of ocular medication and delivery of active agents through many shapes as disclosed respectively by Odrich, Steven, U.S. Patent Application Publication No. 2005/0232972 entitled "Drug Delivery via Punctal Plug"; and Cui, Han. U.S. Pat. No. 9,474,645 entitled "Punctal Plugs for the Delivery of Active Agent," both of which are hereby incorporated by reference herein in their entireties.

Figure 3A:
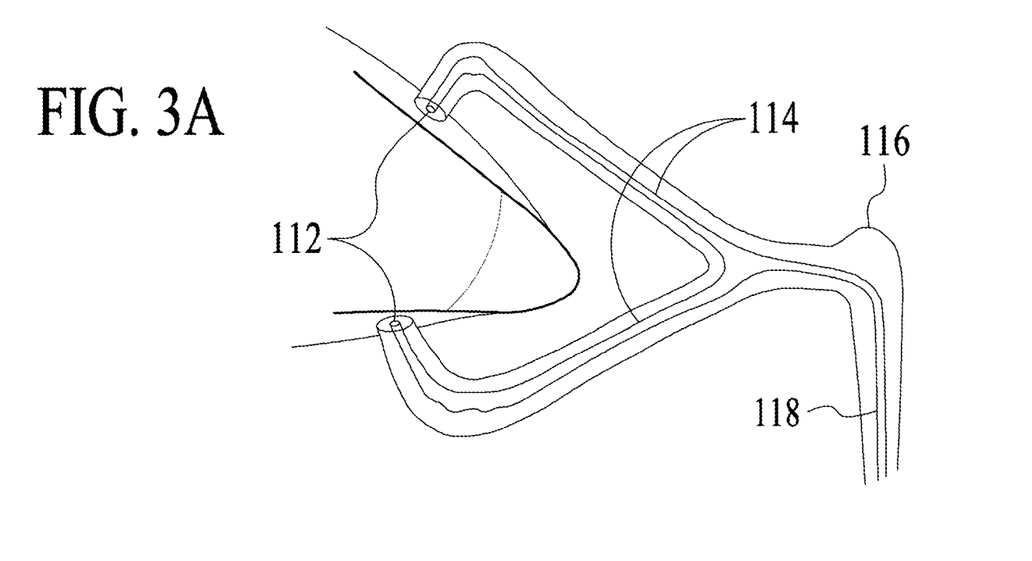
FIG. 3A illustrates components of the tear system without punctal plugs, in accordance with some embodiments.
Figure 3B:
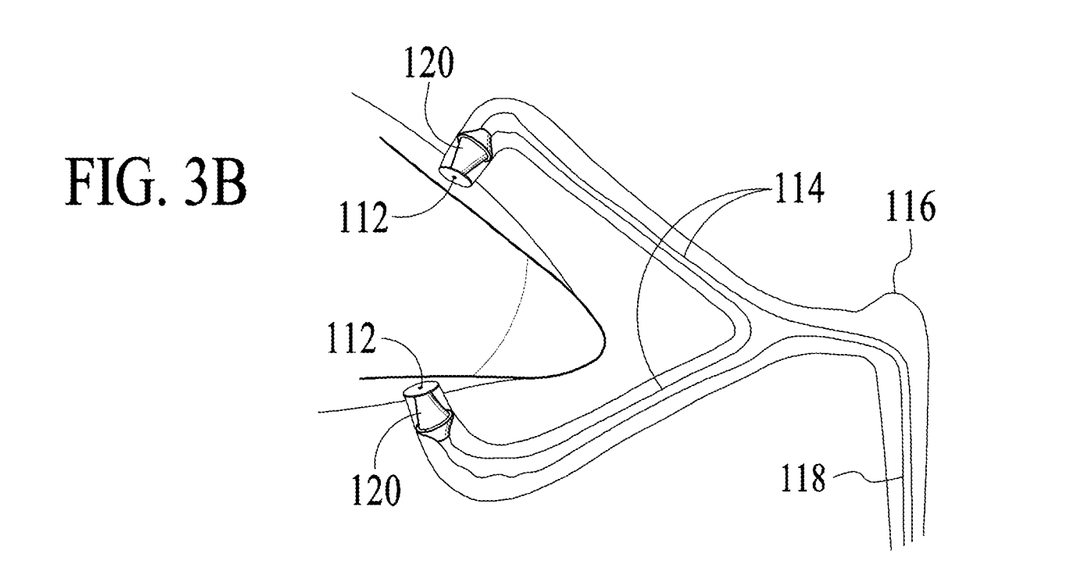
FIG. 3B illustrates components of the tear system with punctal plugs, in accordance with some embodiments.

Generally, the punctal plug 120 may be inserted or placed in one of the lacrimal puncta 112. Referring now to FIG. 3A, a view of the lacrimal puncta 112, lacrimal ducts 114, lacrimal sac 116, and nasolacrimal duct 118 are shown without punctal plugs 120. Referring now to FIG. 3B, a view of the lacrimal puncta 112, lacrimal ducts 114, and lacrimal sac 116 are shown with punctal plugs 120 inserted into the lacrimal puncta 112. It should be noted that, although the following discussion will be drawn to ocular devices inserted into one or both of the lacrimal puncta 112, the location of insertion may not be limited to these. For instance, one or both of the lacrimal puncta 112 may not be functional because of congenital malformation, trauma, or other causes. In such instances or for other reasons, the ocular device could be inserted in the conjunctival sac 108.

Some advantages and benefits of embodiments discussed herein are shown in FIGS. 4A through 4D by illustrating how a punctal plug may be used as a monitoring and/or diagnosis device of medical conditions. In some embodiments, diabetic patients (with or without dry eyes) may have a punctal plug inserted into one or both lacrimal puncta as an easy way to monitor changes their condition (e.g., their glucose levels) in real-time by observing the color to their punctal plug(s) as discussed below. In some embodiments, a punctal plug may be manufactured by injection molding or simple layering (e.g., press-fit).

According to various embodiments, sensor material may be configured and calibrated to detect a compound or substance of interest (hereinafter substance). Although the following discussion will be drawn to PBA and boronic acid chemistry to detect substances, the embodiments herein are not limited to sensor material such as boronic acid but could include any sensor material suitable for the detection of substances such as, without limitation, sugars other than glucose, metal ions, nucleic acids, phospholipids, neurotransmitters, and precursors/metabolites of other macromolecules. In some embodiments, applicable sensor material(s) may be used in eye-care diagnosis of an infection(s) such as, but not limited to, Gram-positive bacterial infection rather than monitoring of substances levels.

Tear biomarkers may be used to detect ocular disease and systemic disease. See Hagan, Suzanne et al., "Tear fluid biomarkers in ocular and system disease: Potential use for predictive, preventive and personalised medicine." The EPMA Journal (2016) 7:15. Tear biomarkers may include proteins such as lysozyme and lactoferrin, lipids, metabolites, cytokines, chemokine, neuromediators, and lacryglobin. Ocular diseases could include dry eye disease, ocular allergy, keratoconus, thyroid-associated orbitopathy, aniridia, glaucoma, trachoma, keratopathy, and diabetic retinopathy. Systemic disease could include cystic fibrosis, scleroderma, and diabetes. Tear biomarkers may be used to detect neurological diseases such as Parkinson disease and multiple sclerosis. Also, tear biomarkers may be used to detect cancers, such as breast, colon, prostate, lung, and ovarian cancer; bacteria, viruses, and fungi. In addition, substances such as drugs, toxins, and hormones may excrete from tears.

Figure 4A:
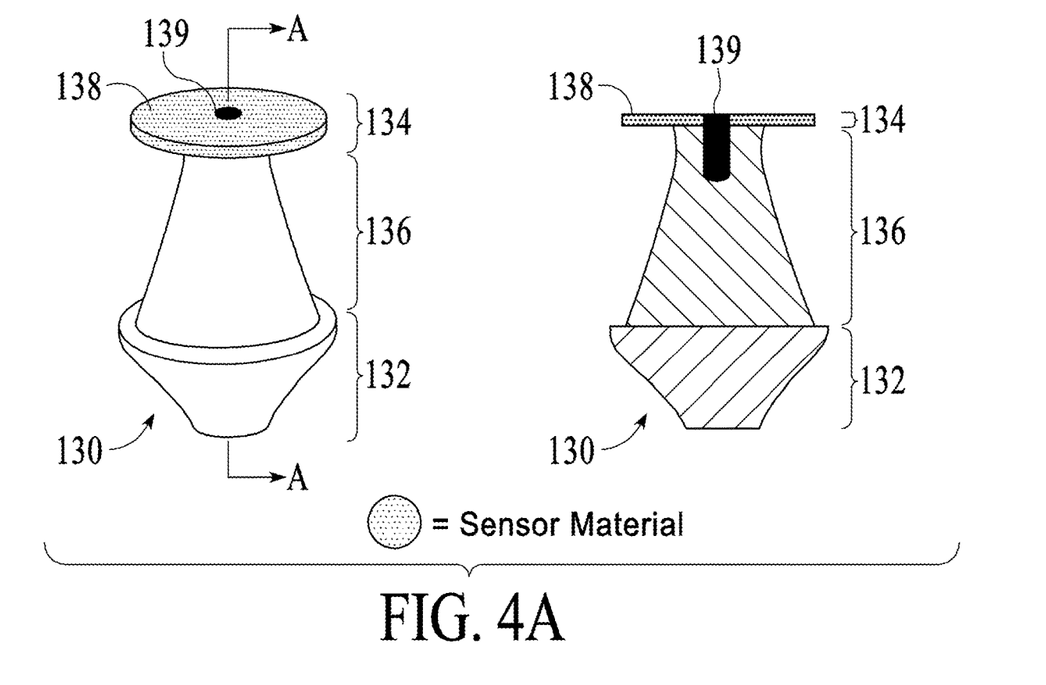
FIG. 4A illustrates an ocular device of which a second region is comprised entirely of a sensor material, in accordance with some embodiments.

Referring now to FIG. 4A through 4D, perspective and cross-sectional views of some embodiments of a punctal plug configured with sensor material are illustrated as being integrated with, or otherwise coupled to a body. Referring now to FIG. 4A, a punctal plug 130 may include first region 132, a second region 134, a body 136, a surface 138 of the second region 134, and a receptacle 139 for an insertion tool, where the second region 134 may be integrated with or otherwise coupled to the body 136. In some embodiments, the second region 134 is comprised entirely of sensor material, where the first region 132 and the body 136 are comprised of non-sensor material. In some embodiments, the entire punctal plug 130 may be coated with or comprised of sensor material.

Figure 4B:
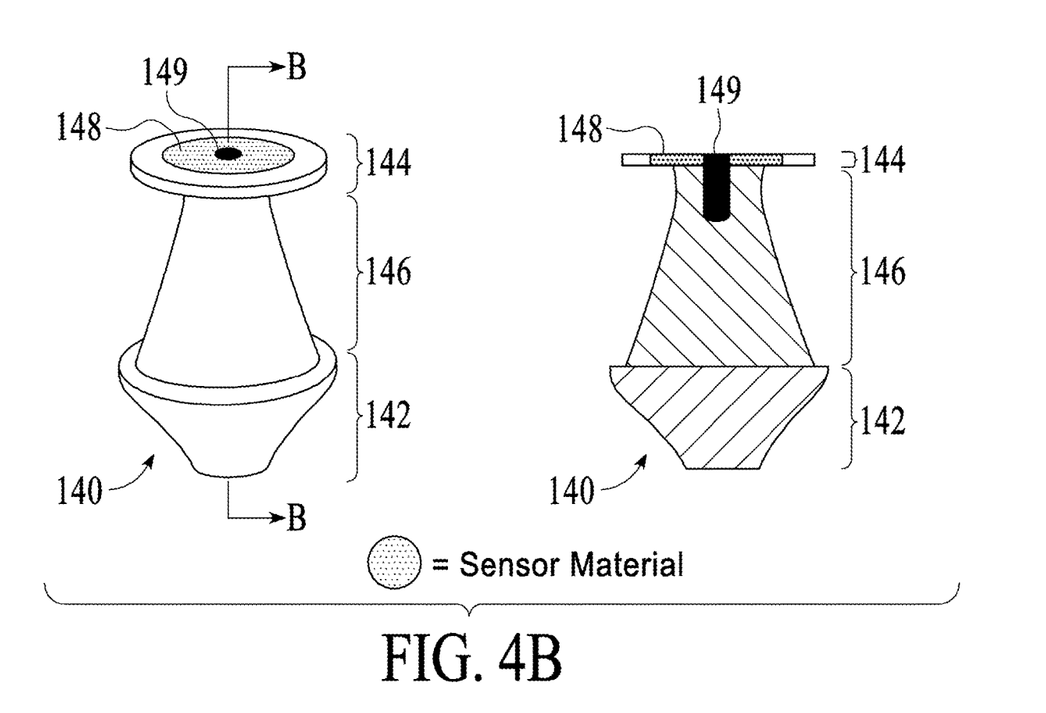
FIG. 4B illustrates an ocular device of which a second region is comprised of sensor and non-sensor materials, in accordance with some embodiments.

Referring now to FIG. 4B, a punctal plug 140 may include a first region 142, a second region 144, a body 146, a surface 148 of the second region 144, and an insertion tool receptacle 149, where the second region 144 may be comprised of sensor and non-sensor materials. In some embodiments, the non-sensor material may be the same material as the first region 142 and/or the body 146. In some embodiments, the entire punctal plug 140 may be coated with or comprised of sensor material.

Figure 4C:
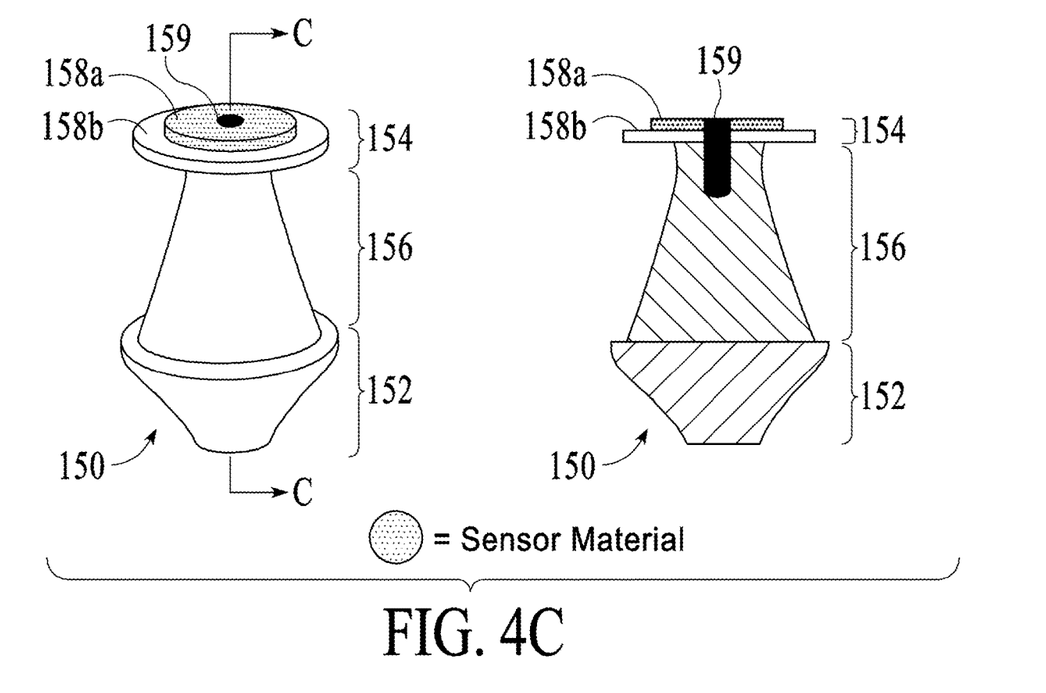
FIG. 4C illustrates an ocular device of which a second region is comprised of two tiers, where one tier is comprised of a sensor material, in accordance with some embodiments.

Referring now to FIG. 4C, a punctal plug 150 may include a first region 152; a second region 154 having an upper tier and a lower tier; a body 156; surfaces 158a and 158b of the upper and lower tiers, respectively; and an insertion tool receptacle 159, where the upper and lower tiers may be comprised of sensor and non-sensor materials, respectively. In some embodiments, the entire punctal plug 150 may be coated with or comprised of sensor material.

Figure 4D:
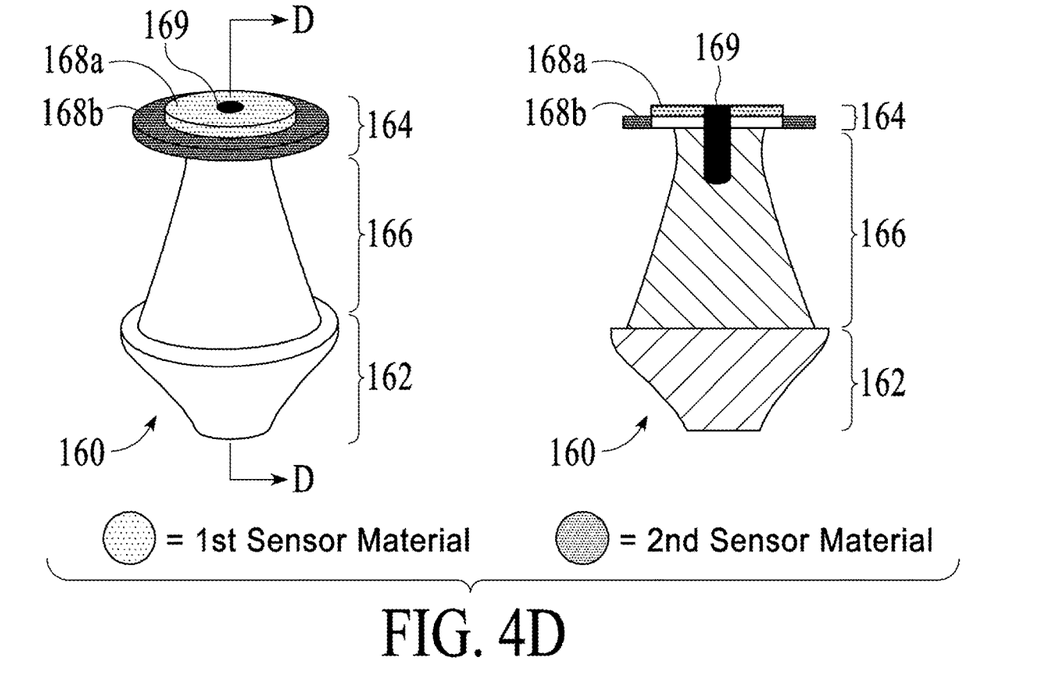
FIG. 4D illustrates an ocular device of which a second region is comprised of two tiers, where a first tier is comprised of one sensor material and a second comprised of a second sensor material, in accordance with some embodiments.

Referring now to FIG. 4D, a punctal plug 160 may include a first region 162; a second region 164 having an upper tier and a lower tier; a body 166; surfaces 168a and 168b of the upper and lower tiers, respectively; and an insertion tool receptacle 169, where the upper tier may have color which is visually conspicuous from a color of the lower tier comprised of sensor and/or non-sensor materials, respectively, where the color of the sensor material(s) may change from a baseline color during normal conditions to another visually conspicuous color with a detection of an abnormal condition such as, for example, abnormal glucose levels or indication of an infection. In some embodiments, the baseline color or changes thereto made be readily visible to a third-party observer and/or the patient looking through a mirror.

As described in Braun, the color change is associated with a matrix of embedded boronic acid derivative(s) which causes the material to swell upon interaction with the substances. By varying the dispersion of the boronic acid within the matrix, a specific substance threshold may be calibrated to induce the desired color change at a prescribed level with a target compound. In some embodiments, the sensor material could be white or clear, so that relative changes in color may be readily observable.

As described in Lane, patients in one study that were diagnosed with type-2 diabetes typically had a fasting blood glucose level of about 10 millimoles per liter (mmol/L). After a meal, this blood glucose level rose to about 16 mmol/L after the first thirty minutes, a precursor for hyperglycemia. This correlated to an increase from 0.1 mmol/L to 0.3 mmol/L in tear glucose the same thirty minutes. If a 0.25 mmol/L tear glucose level is set as a threshold, the sensor material may be calibrated to provide a color indication commensurate with and/or proportional to levels exceeding the threshold of the baseline color. In contrast, non-diabetics in the study showed blood glucose increasing from about 6 mmol/L to about 9 mmol/L thirty minutes after the same meal, where tear glucose maintained a steady level of about 0.1 mmol/L which is below the threshold and indicated by no change of the baseline color.

Figure 5A:
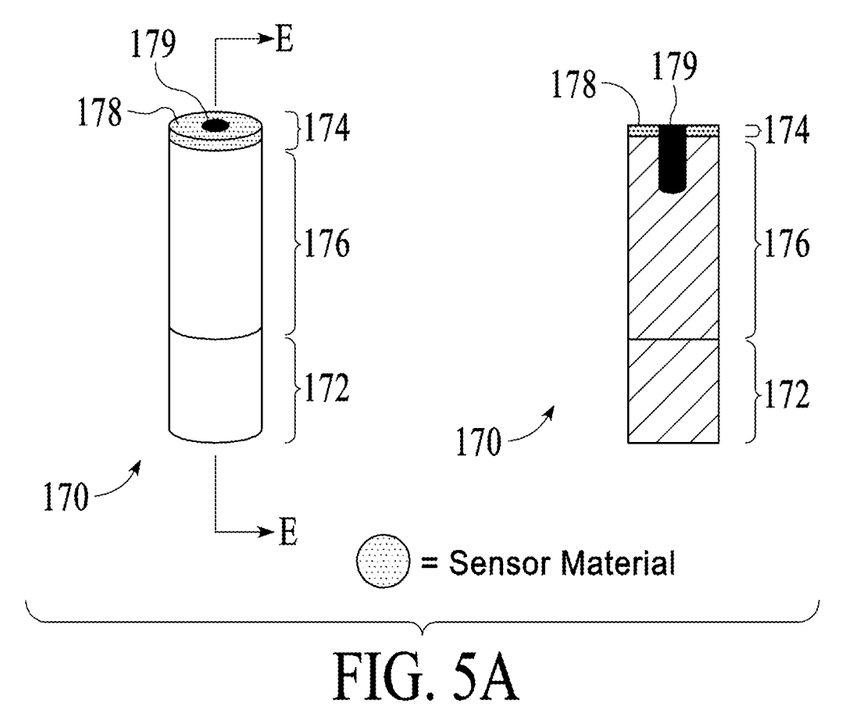
FIG. 5A illustrates an ocular device of which a second region is comprised entirely of radiation-responsive sensor material, in accordance with some embodiments.
Figure 5B:
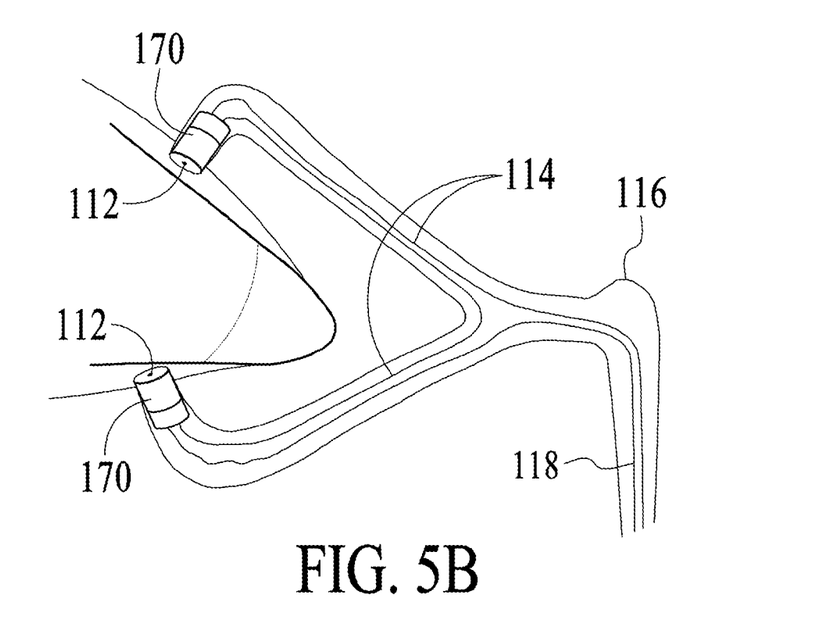
FIG. 5B illustrates components of the tear system with the ocular devices of FIG. 5A, in accordance with some embodiments.
Figure 5C:
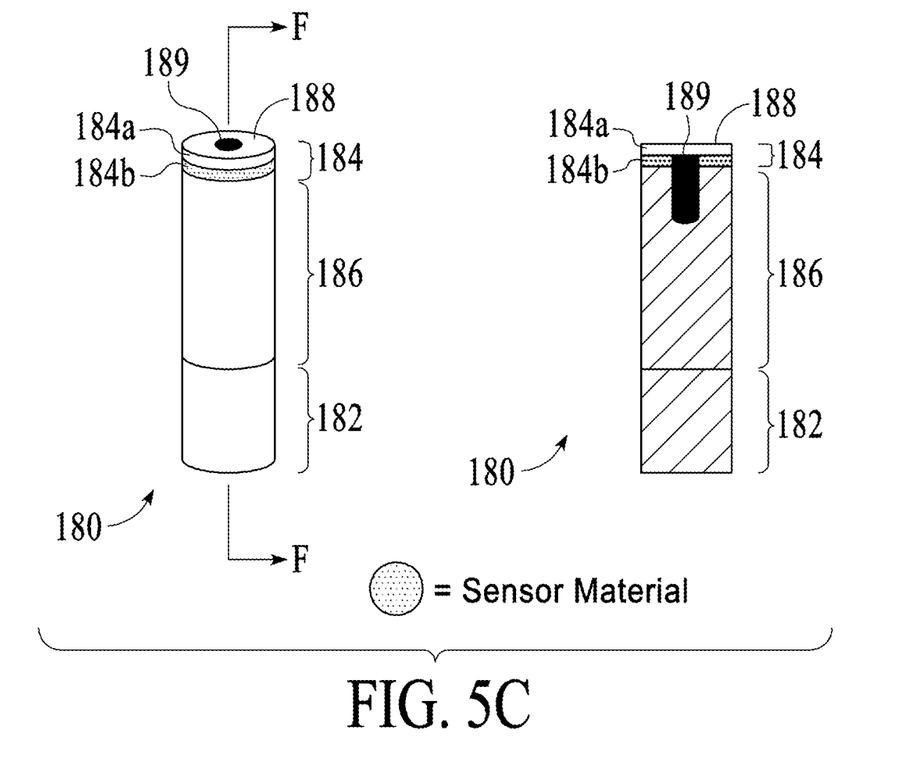
FIG. 5C illustrates an ocular device of which a portion of a second region is comprised of radiation-responsive sensor material, in accordance with some embodiments.

Referring now to FIG. 5A through 5C, perspective and cross-sectional views of some embodiments of a punctal plug configured with radiation-responsive sensor material are illustrated integrated with, or otherwise coupled to a body. Radiation-responsive sensor material could include materials which emit visible or near-infrared radiation of different wavelengths (i.e., different colors) of the electromagnetic spectrum when excited (or irradiated) with radiation from a source providing a different wavelength of the electromagnetic spectrum. The radiation may be visible or non-visible (such as ultraviolet). In some embodiments, the sensor material may be excited with radiation passing through the lower and/or upper eyelids 104 and 106, respectively; that is, the sensor material being excited with a patient's eyes closed. Such approach may be employed with the other variations of the ocular device described herein.

In some embodiments, the radiation-responsive sensor material could include molecules whose fluorescence intensity or wavelength may provide an indication of the chemical composition of a person's tears. Fluorescent molecules may detect chemicals relevant to tear fluid. See Yetisen, Ali et al., "Paper-based Microfluidic System for Tear Electrolyte Analysis." Lap Chip, 2017, 17, 1137 (Yetisen), which is hereby incorporated by reference herein in its entirety.

Referring now to FIG. 5A, a punctal plug 170 may include first region 172, a second region 174, a body 176, a surface 178 of the second region 172, and a receptacle 179 for an insertion tool, where the second region 174 may be integrated with or otherwise coupled to the body 176. In some embodiments, the second region 174 is comprised entirely of sensor material, where the first region 172 and the body 176 are comprised of non-sensor material. In some embodiments, visible or near-infrared radiation may be emitted through the sides of the plug 170 in addition or as an alternative to being emitted through the surface 178.

The punctal plug 170 may be inserted in one or both of the lacrimal puncta 112. Referring now to FIG. 5B, a view of the lacrimal puncta 112, lacrimal ducts 114, and lacrimal sac 116 are shown with punctal plugs 170 inserted into the lacrimal puncta 112.

Referring now to FIG. 5C, a punctal plug 180 may include first region 182, a second region 184 having an upper region 184a and a lower region 184b, a body 186, and outer surface 188, and an insertion tool receptacle 159. In some embodiments, the upper region 184a could be comprised of a non-sensor, translucent material that may not noticeable to an observer of the punctum but allows radiation to pass through to the lower region comprised of sensor material. In some embodiments, visible or near-infrared radiation may be emitted through the sides of the plug 180.

Some advantages and benefits of embodiments discussed herein are shown in FIGS. 6A through 6D by illustrating how ocular devices including contact lenses may be used as a monitoring and/or diagnosis device of medical conditions. In some embodiments, two components may be coupled to one another in any suitable manner, such as by placing the boronic acid derivatives in a matrix composed of hydrogel, a common material used in the production of contact lenses. In some embodiments, the sensor material could be directly incorporated into the lens and isolated to a variety of convenient shapes. In some embodiments, the sensor material could be disposed over the entirety of the contact lens; over select portions or surfaces thereof such as, for example, at one or more sides or edges of the lens to generally cover the whites of a user's eye); or in other regions of the lens.

When a prescribed level of a target compound (e.g., high glucose levels) is detected in the user's tears, the color of the sensor material could change to one that contrasts with the color of the user's eyes so that the color change may be observable by a third party and/or wearer of the contact lenses. In some embodiments, the color of the sensor material can be configured to change from a baseline color during normal conditions to another color in abnormal conditions. The sensor material can be configured to be clear or white, for example, to match the color of the patient's iris or a cosmetically desired color when the condition of interest is not present, and a different color in the abnormal condition.

For example, the color of the sensor material configured to be responsive to changes in tear glucose levels could be transparent when glucose levels are normal, and may be configured to have visible color changes (e.g., purple or pink) if the glucose levels are abnormal, providing a visual warning to the patient. In some embodiments, if the sensor material is placed in a region where it is visible if not transparent, then the user could receive a clear indication of the change in glucose levels. In some embodiments, if the sensor material is located in an area not visible to the user (e.g., the margin of the contact lens on the sclera), then a change in color may be visible to others looking at the user's eyes or to the user if looking in a mirror.

Figure 6A:
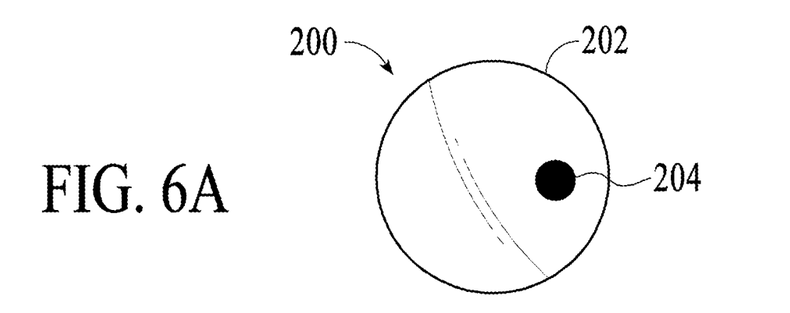
FIGS. 6A-6D illustrate an ocular device of exemplary contact lenses that include multiple sensor materials coupled thereto, in accordance with various embodiments of the present invention.
Figure 6B:
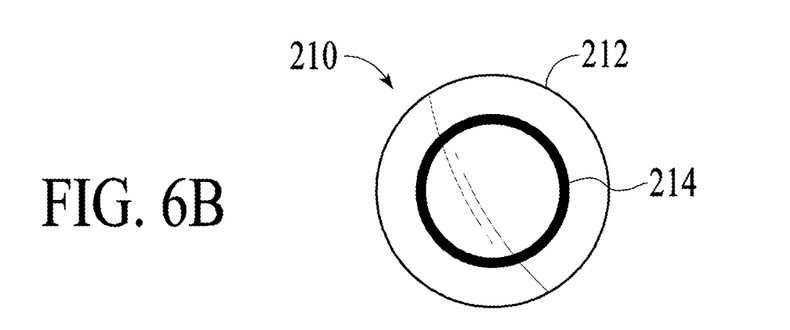
Figure 6C:
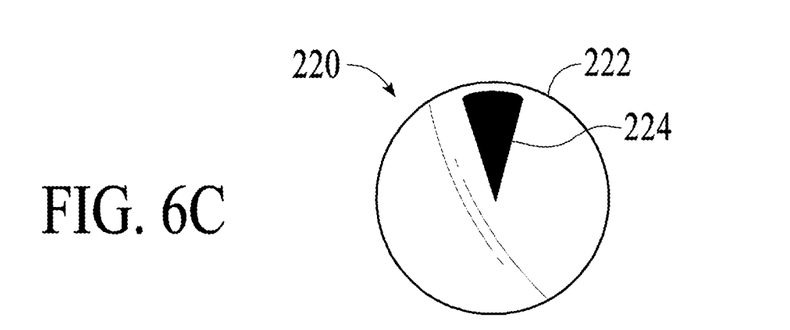

Referring to FIG. 6A, an ocular device 200 could include a contact lens 202 and sensor material 204 configured in the shape of a dot. Referring to FIG. 6B, an ocular device 210 could include a contact lens 212 and sensor material 214 configured in the shape of ring concentric to the contact lens 212. Referring to FIG. 6C, an ocular device 220 could include a contact lens 222 and sensor material 224 configured in the shape of a wedge that, at least, partially overlays the pupil. With the wedge configuration, a patient could be provided with a direct visual cue upon change from transparent to visible color, advantageously circumventing use of a mirror.

Figure 6D:
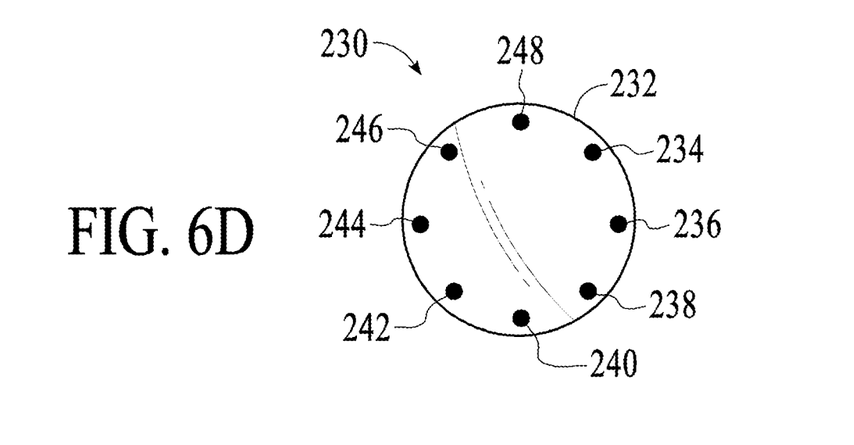

Referring to FIG. 6D, an ocular device 230 could include a contact lens 232 and sensor materials 234 through 248 configured in multiple regions to detect multiple chemicals in the tears to monitor multiple conditions. In some embodiments, the sensor materials 234 through 248 may be specifically calibrated to a variety of substances for boronic acid to exhibit different colors as described above and allow for multiple continuous monitoring and/or diagnoses simultaneously. It should be noted that, although eight sensor materials 234 through 248 are illustrated, any suitable number of sensor materials could be configured on coupled to the contact lens 232.

While the discussion above was primarily drawn to ocular devices in the form of a plug or contact lens, the ocular device comprising sensor material may come in other forms known to those skilled in the art suitable for placement into the eye on a temporary or semi-permanent basis, such as test strips.

As used herein, the term "embodiment" means an embodiment that serves to illustrate by way of example but not limitation.

It will be appreciated to those skilled in the art that the preceding examples and embodiments are exemplary and not limiting to the broad scope of the inventive concepts disclosed herein. It is intended that all modifications, permutations, enhancements, equivalents, and improvements thereto that are apparent to those skilled in the art upon a reading of the specification and a study of the drawings are included within the broad scope of the inventive concepts disclosed herein. It is therefore intended that the following appended claims include all such modifications, permutations, enhancements, equivalents, and improvements falling within the broad scope of the inventive concepts disclosed herein.

What is claimed is:

1. An ocular device, comprising:
   a device configured for placement into a lacrimal punctum or lacrimal punctum and canaliculus of a person, where the device includes at least one sensor material responsive to at least one component of a chemical composition of the person's tears, where
   each one sensor material is configured to present a tear-based color from a plurality of tear-based colors indicative of a medical condition of the person, wherein the tear-based color is visible to the human eye;
   wherein the device is a punctal insert;
   wherein the tear-based color is visible through the person's closed eyelid; and
   wherein at least one sensor material is configured to display a tear-based color when exposed to a specific, or family of, bacteria, virus, or fungus or biomarkers of a specific, or family of, bacteria, virus, fungus, or non-communicable disease in tears.

2. The ocular device of claim 1, wherein at least one sensor material is comprised of phenylboronic acid.

3. The ocular device of claim 1, wherein at least one sensor material is comprised of a material that emits at least a first radiation within a first range of visible wavelengths of the electromagnetic spectrum when excited by at least a second radiation within a second range of wavelengths of the electromagnetic spectrum, wherein the emitted radiation is visible to the human eye.

4. The ocular device of claim 3, wherein the plurality of tear-based colors is a plurality of colors of the first radiation emitted when the sensor material is excited by the second radiation.

5. The ocular device of claim 1, wherein
   at least one tear-based color of the plurality of tear-based colors indicates a normal medical condition of the person, and
   at least one tear-based color of the plurality of tear-based colors indicates an abnormal medical condition of the person.

6. The ocular device of claim 1, wherein the device includes a sensor region in which at least a portion of at least one surface of the sensor region includes the at least one sensor material.

7. The ocular device of claim 6, wherein the at least one surface is one surface.

8. The ocular device of claim 7, wherein the at least one portion of the one surface is the entire surface.

9. The ocular device of claim 6, wherein
   the at least one surface is a plurality of tiered surfaces,
   at least a portion of one of the plurality of tiered surfaces is configured with a first sensor material, and
   at least a portion of another of the plurality of tiered surfaces is configured with a second sensor material.

10. The ocular device of claim 1, wherein substantially the entire device is comprised of or coated with sensor material.

11. The ocular device of claim 1, wherein the tear-based color is based on a wavelength-dependent absorbance, wavelength-dependent reflectivity, or wavelength-dependent light emission of at least one sensor material.

12. The ocular device of claim 11, wherein the sensor material that exhibits absorbance is comprised of plasmonic nanoparticles or light-absorbing dye.

13. The ocular device of claim 11, wherein the sensor material that reflects is comprised of a polymerized crystalline colloidal array.

14. The ocular device of claim 11, wherein the sensor material that emits light is comprised of a fluorescent dye, fluorescent quantum dots, fluorescent particles, or photoluminescent nanoparticles.

15. The ocular device of claim 1, wherein the intensity of said tear-based color indicates that the at least one sensor material is exposed to a specific, or family of, bacteria, virus, or fungus or biomarkers of a specific, or family of, bacteria, virus, fungus, or non-communicable disease in tears.

16. The ocular device of claim 1, wherein the spectral distribution of said tear-based color indicates that the at least one sensor material is exposed to a specific, or family of, bacteria, virus, or fungus or biomarkers of a specific, or family of, bacteria, virus, fungus, or non-communicable disease in tears.

17. The ocular device of claim 1, wherein the punctal insert is a punctal plug.

18. An ocular device method, comprising:
placing a device into a lacrimal punctum or lacrimal punctum and canaliculus of a person, where
the device includes at least one sensor material responsive to at least one component of the person's tears, where
each one sensor material is configured to present a tear-based color from a plurality of tear-based colors indicative of a medical condition of the person, wherein the tear-based color is visible to the human eye or is in the range of near-infra red;
wherein the device is a punctal insert;
wherein the tear-based color is visible through the person's closed eyelid; and
wherein at least one sensor material is configured to display a tear-based color when exposed to a specific, or family of, bacteria, virus, or fungus or biomarkers of a specific, or family of, bacteria, virus, fungus, or non-communicable disease in tears.

19. The ocular device method of claim 18, wherein at least one sensor material is comprised of phenylboronic acid.

20. The ocular device method of claim 18, wherein at least one sensor material is comprised of a material that emits at least a first radiation within a first range of wavelengths of the electromagnetic spectrum when excited by at least a second radiation within a second range of wavelengths of the electromagnetic spectrum.

21. The ocular device method of claim 20, wherein the plurality of tear-based colors is a plurality of colors of the first radiation emitted when the sensor material is excited by the second radiation.

22. The ocular device method of claim 20, wherein the intensity of the emitted radiation is detectable by the naked eye only when a target compound, ion, or biomarker exceeds a prescribed range of concentrations in tear fluid.

23. The ocular device method of claim 18, wherein
at least one tear-based color of the plurality of tear-based colors indicates a normal medical condition of the person, and
at least one tear-based color of the plurality of tear-based colors indicates an abnormal medical condition of the person.

24. The ocular device method of claim 18, wherein the device includes a sensor region in which at least a portion of at least one surface of the sensor region includes the at least one sensor material.

25. The ocular device method of claim 24, wherein the at least one surface is one surface.

26. The ocular device method of claim 25, wherein the at least a portion of the one surface is the entire surface.

27. The ocular device of claim 25, wherein
the at least one surface is a plurality of tiered surfaces,
at least a portion of one of the plurality of tiered surfaces is configured with a first sensor material, and
at least a portion of another of the plurality of tiered surfaces is configured with a second sensor material.

28. The ocular device method of claim 18, wherein substantially the entire device is comprised of or coated with the at least on sensor material.

29. The ocular device method of claim 18, wherein a specific substance threshold is calibrated to induce a desired color change at a prescribed range of concentrations with a target compound, ion, or biomarker.

30. An ocular device method, comprising:
observing at least one tear-based color presented by a device placed into a lacrimal punctum or lacrimal punctum and canaliculus_of a person to determine at least one medical condition of the person, where
the device includes at least one sensor material responsive to at least one component of the person's tears, where
each one sensor material is configured to present a tear-based color from a plurality of tear-based colors indicative of a medical condition of the person, wherein the tear-based color is visible to the human eye or to a near-infra red detector;
wherein the device is a punctal insert;
wherein the tear-based color is visible through the person's closed eyelid; and
wherein at least one sensor material is configured to display a tear-based color when exposed to a specific, or family of, bacteria, virus, or fungus or biomarkers of a specific, or family of, bacteria, virus, fungus, or non-communicable disease in tears.

31. The ocular device method of claim 30, wherein at least one sensor material is comprised of phenylboronic acid.

32. The ocular device method of claim 30, wherein the sensor material is comprised of a material that emits at least a first radiation within a first range of wavelengths of the electromagnetic spectrum when excited by at least a second radiation within a second range of wavelengths of the electromagnetic spectrum.

33. The ocular device method of claim 32, wherein at least one sensor material is comprised of a material that emits first radiation of the electromagnetic spectrum when excited by second radiation of the electromagnetic spectrum.

34. The ocular device method of claim 33, wherein the first radiation is at least partially visible through the person's eyelid.

35. The ocular device method of claim 33, wherein the first radiation is measurable through the person's eyelid.

36. The ocular device method of claim 30, wherein
at least one color of the plurality of colors indicates a normal medical condition of the person, and
at least one color of the plurality of colors indicates an abnormal medical condition of the person.

37. The ocular device method of claim 30, wherein substantially the entire device is comprised of or coated by the at least one sensor material.

38. An ocular device, comprising:
a device configured for placement into a lacrimal punctum or lacrimal punctum and canaliculus of a person, where
the device includes at least one sensor material responsive to at least one component of a chemical composition of the person's tears, where each one sensor material is configured to exhibit a tear-based change in light emission or light reflectance indicative of a medical condition of the person;

wherein the device is a punctal insert; and wherein the intensity of said emitted or reflected light indicates that the at least one sensor material is exposed to a specific, or family of, bacteria, virus, or fungus or biomarkers of a specific, or family of, bacteria, virus, fungus, or non-communicable disease in tears.

39. The ocular device of claim 38, wherein the emitted or reflected light is in the range of infra-red.

40. The ocular device of claim 39, wherein the spectral distribution of said emitted or reflected light indicates that the at least one sensor material is exposed to a specific, or family of, bacteria, virus, or fungus or biomarkers of a specific, or family of, bacteria, virus, fungus, or non-communicable disease in tears.

41. The ocular device of claim 38, wherein the emitted or reflected light is detectable through the patient's eyelid using an infra-red sensing device.

\* \* \* \* \*